United States Patent [19]
Whalen et al.

[11] Patent Number: 5,374,243
[45] Date of Patent: Dec. 20, 1994

[54] OXYGEN PERMEABLE BAG CONTAINING OXYGEN-TRANSPORTING PERFLUOROCHEMICAL FOR PROVIDING OXYGEN INTERNALLY TO MAMMALS

[75] Inventors: John J. Whalen, Pasadena; Charles M. Heldebrandt, Arcadia, both of Calif.

[73] Assignee: Alpha Therapeutic Corporation, Los Angeles, Calif.

[21] Appl. No.: 85,920

[22] Filed: Jul. 6, 1993

[51] Int. Cl.$^5$ .............................................. A61M 37/00
[52] U.S. Cl. ........................................ 604/23; 604/24; 604/892.1; 604/891.1; 128/898
[58] Field of Search ............... 604/890.1, 891.1, 892.1, 604/23, 25, 27, 29, 96, 280; 623/12, 26; 128/898, 200.25; 606/191–194

[56] References Cited

U.S. PATENT DOCUMENTS

| | | |
|---|---|---|
| 3,940,802 | 3/1976 | Sako et al. |
| 4,416,267 | 11/1983 | Gowen et al. ........................ 128/898 |
| 4,437,856 | 3/1984 | Valli ....................................... 604/29 |
| 4,450,841 | 5/1984 | Osterholm ............................ 128/898 |
| 4,923,457 | 5/1990 | Ellingsen ........................... 604/891.1 |
| 4,925,446 | 5/1990 | Gorau et al. ....................... 604/891.1 |
| 4,963,130 | 10/1990 | Osterholm ............................. 604/24 |
| 4,969,869 | 11/1990 | Burgir et al. ........................... 604/23 |
| 5,112,303 | 5/1992 | Pundenz et al. .................. 604/891.1 |

FOREIGN PATENT DOCUMENTS 0081118   3/1983   European Pat. Off. ....... 128/200.25

OTHER PUBLICATIONS

Japanese Journal of Surgery, vol. 21, No. 6, pp. 661–668, 1991.
Br. J. Surg, 1987, vol. 74, pp. 137–139.
Br. J. Anaesth., (1984), No. 8, pp. 867–872, vol. 56.

*Primary Examiner*—C. Fred Rosenbaum
*Assistant Examiner*—Chalin Smith
*Attorney, Agent, or Firm*—Sughrue, Mion, Zinn, Macpeak & Seas

[57] ABSTRACT

A method for providing oxygen to an internal body cavity by providing an oxygenated oxygen-transporting perfluorochemical enclosed within an oxygen permeable/perfluorochemical impermeable membrane within said body cavity.

13 Claims, No Drawings

OXYGEN PERMEABLE BAG CONTAINING OXYGEN-TRANSPORTING PERFLUOROCHEMICAL FOR PROVIDING OXYGEN INTERNALLY TO MAMMALS

FIELD OF THE INVENTION

The present invention relates to methods for providing oxygen to internal tissues of a mammal. More specifically, the invention provides methods allowing the utilization of oxygen-transporting perfluorochemicals for supplying oxygen to body tissues associated with the peritoneal cavity or gastrointestinal tract of a patient.

BACKGROUND OF THE INVENTION

Martin, et al., "Experimental Studies on the Prediction and Prevention of Stress Ulcers Using Tonometry, Reflectance Spectrophotometry and Oxygenated Perfluorochemicals," *Japanese Journal of Surgery*, Vol. 21, No. 6, page 661 (1991), have investigated whether oxygenated perfluorochemicals protect the gastric mucosa against hemorrhage-induced stress ulcerations. Prior to their work, it had been reported by others that a close correlation existed between the occurrence of stress ulcers and the degree of gastric mucosal ischemia resulting in a decreased intramural pH. Using a dog model, Martin, et al. treated one group by lavaging the stomach with a modified Fluosol®-DA 20% emulsion. Fluosol®-DA was obtained from The Green Cross Corporation, Osaka, Japan, and contains the oxygen-transporting perfluoro-chemicals perfluorodecalin and perfluorotri-n-propylamine. The Fluosol®-DA emulsion was oxygenated by bubbling with 100% oxygen. Lavage was commenced when the gastric intramural pH decreased to 7.24 following hemorrhagic shock, which pH level was considered to be the critical level of ischemia, and was terminated just before reinfusion of the shed blood. Martin, et al. describe their results as indicating that local application of Fluosol®-DA can increase tissue oxygen saturation of the stomach during shock and can also protect the mucosa against acute ulceration. The severity of macroscopic gastric mucosal lesions in the oxygenated Fluosol®-DA treated group was stated to be significantly less than that of two control groups.

The method of Martin, et al., although potentially offering therapeutic benefit, is impractical. The preparation of oxygen-containing emulsions is a labor-intensive endeavor. Thus far, there has not been a truly cost-effective method by which existing oxygen carrying emulsions could be used to practice the method of Martin, et al. Although the practitioner might then theorize the use of neat perfluorochemical liquids in the process of Martin, et al., there are possible problems with the administration of neat perfluorochemicals to the mammalian gastrointestinal tract. In both the gastrointestinal tract and peritoneal cavity, there is the potential for introduction of the neat perfluoro-chemical into the vascular system through the presence of large or small ulcerations or abrasions or other connection between the gastrointestinal tract or the peritoneal cavity and the vascular system. The safety of neat perfluorochemical introduced into the vascular system cannot be presumed. Further, the long term exposure of internal body cells to neat perfluorochemicals has not been established.

Polymeric balloons or bags inflated with saline have been tried as intragastric devices to aid in weight reduction for obese patients. Latex balloons failed within a few weeks, while silicone elastomer balloons maintained their volume for one year and longer. See McFarland, et al., "The intragastric balloon: a novel idea proved ineffective," *British Journal of Surgery*, Vol. 74, No. 2, page 137 (1987). McFarland, et al. describe a method for inserting into the stomach an empty balloon with a connected fill tube through which liquid can be passed into the balloon. Once the balloon reached the stomach under fluoroscopic guidance, Conray 280 (May and Baker) was inserted into the balloon through the fill tube for clear identification.

Fluosol®-DA is now commercially available to the medical profession in the United States from Alpha Therapeutic Corporation of Los Angeles, Calif., and is supplied in a plastic bag which is gas permeable, but impermeable to most liquids. Indeed, Fluosol®-DA is not supplied oxygenated because oxygen in the bag could diffuse out through the plastic bag and nitrogen or other gas in the air could diffuse into the plastic bag to reach equilibrium. Such a bag is a MEDIDEX brand bag provided by Nariwa Rubber Company, Nara, Japan, formed of a polyvinyl chloride containing a polyester polyurethane plasticizer as described in U.S. Pat. No. 3,940,802.

U.S. Pat. No. 4,963,130 by Osterholm describes the intra-peritoneal perfusion of an oxygenated fluorocarbon as an artificial lung. In this instance, the oxygenated fluorocarbon liquid is circulated through the peritoneal cavity for general body oxygenation. Osterholm recognizes certain disadvantages in the practice of this method, noting that steps may need to be taken to minimize the incidence of peritoneal infection, and that the neat fluorocarbon is not preferred because, following completion of treatment, a lavage should be administered to wash remaining fluorocarbon from the peritoneum.

Similarly, Faithful, et al., "Whole Body Oxygenation Using Intraperitoneal Perfusion of Fluorocarbons," *B. J. Anaesth.*, 56, page 867 (1984), continuously pumped oxygenated Fluosol®-DA emulsion into the peritoneal cavities of rabbits and reported that extra pulmonary oxygenation using peritoneal lavage was feasible. However, the authors noted potential problems with the whole body approach, namely, the question of possible oxygen toxicity of the peritoneal surfaces and degree of absorption of the fluorocarbons, possibly leading to hepatic toxicity. Thus, another problem in utilizing perfluorocarbons as oxygen-transporting systems within the cavities of the body is to develop a means in which to control the amount of oxygen discharged over time from the fluorochemical for availability by the body.

SUMMARY OF THE INVENTION

The present invention is directed to a method for providing oxygen into the peritoneal cavity or the gastrointestinal (GI) tract of a mammal, preferably a human.

In the method of the present invention, an oxygenated oxygen-transporting perfluorochemical formulation enclosed within an oxygen/carbon dioxide permeable, perfluorochemical impermeable membrane is inserted into the GI or peritoneal cavity.

In one embodiment of the present invention, a perfluorochemical emulsion formulation is employed.

In another embodiment of the present invention, a neat perfluorochemical is employed.

In each of the above embodiments, the membrane enclosing the perfluorochemical emulsion or the neat perflurochemical is selected to prevent or minimize passage of perfluorochemical therethrough so that the perfluorochemical does not directly contact body tissue.

Further, in each of the above embodiments, the perfluorocarbon formulation is oxygenated to saturation or at least to a pressure sufficient to allow passage of oxygen out of the emulsion membrane, which can be in the form of a bag or balloon or pouch, and to allow passage of carbon dioxide into the enclosure formed by the membrane.

Where desired, various nutrients such as vitamins, glucose and amino acids which can pass through the oxygen permeable membrane are included within the perfluorocarbon formulation, which then is preferably an emulsion, for providing the same to the patient.

DETAILED DESCRIPTION OF THE INVENTION

The bag, balloon or pouch (hereinafter "bag") to be inserted into the peritoneal cavity or the gastrointestinal tract of a patient and which will contain the oxygen-transporting perfluorochemical must be permeable to oxygen and carbon dioxide and impermeable to the liquid perfluorochemical. Further, the material forming the bag must be resistant to the environment of the internal body cavity which will surround it during usage, such as the highly acidic environment of the stomach, and otherwise also be biocompatible.

It is known that semi-permeable and porous membranes permeable to oxygen and impermeable to liquids can be constructed of various natural and synthetic materials, any of which can be selected for use herein as long as it meets the aforementioned general requirements of biocompatibility and environmental stability. For example, semi-permeable membranes are known formed of polytetrafluoroethylene, polysilicon, polypropylene, polyethylene, polysulfone, polyacrylnitrile, polyethyleneterephthalate, polybutyleneterephthalate, polycarbonate, polyurethane, 6,6-nylon, 6-nylon and cellulose acetate. A porous membrane could also be used in the practice of the present invention as long as appropriate pressure is maintained. Porous membrane materials are disclosed in U.S. Pat. No. 3,651,616. A porous membrane is one in which a gas passes through the membrane merely by following the path of the pores and not by diffusion through the material as in the case of permeable membranes. The pore size is selected to be smaller than that of the molecules of the liquid. Typically, a porous membrane has pores with an apparent diameter of about 0.01–3 microns, preferably 0.05–1.5 microns and a critical surface tension (a measure of the wetability of a solid mass on its surface) of less than 40 dynes/cm at 20° C. or in any event less than the surface tension of the perfluorochemical liquid. The following perfluoro compounds can be used alone or in combination to practice the present invention and can be contained in an emulsion in, for example, an amount of about 10 to 50% (W/V) or used in the neat state:

Perfluorocarbons useful herein include those having about 9 to 11 carbon atoms, such as a perfluorocycloalkane or perfluoroalkylcycloalkane which includes, for example, perfluoromethylpropylcyclohexane, perfluorobutylcyclohexane, perfluorotrimethylcyclohexane, perfluoroethylpropylcyclohexane, perfluorodecalin and perfluoromethyldecalin; a perfluoro $C_{4-7}$-alkyltetrahydropyran such as perfluorohexyltetrahydropyran, perfluoro pentyltetrahydrofuran, perfluoro hexyltetrahydrofuran and perfluoro heptyltetrahydrofuran; and a perfluoroalkane having about 9–11 carbon atoms such as perfluorononane and perfluorodecane. Other perfluorocarbons useful herein include, e.g., perfluoro $C_{9-18}$ polycyclic compounds such as bicyclononanes, methyl and dimethyl bicyclooctanes, pinane, camphane, adamantane and alkyl($C_{1-6}$) adamantanes such as dimethyladamantane, ethyl adamantane, and the like. Other heterocyclic perfluorocarbons useful herein include perfluoro saturated and N-alkyl-substituted quinolines, quinolizines, quinolidines, pyrrolidines and morpholines.

Other useful perfluorocarbons include perfluoro tert-amines having about 9 to 11 carbon atoms such as perfluoro tert-alkylamines having 9 to 11 carbon atoms which includes, for example, perfluorotrialkylamines such as perfluoro N, N-diethylpentylamine, perfluoro N, N-diethylhexylamine, perfluoro N, N-dipropylbutylamine and perfluorotripropylamine having 9–11 carbon atoms such as perfluoro N, N-diethylcyclohexylamine; a perfluoro N-$C_{4-6}$-alkylpiperidine such as perfluoro N-pentylpiperidine, perfluoro N-hexylpiperidine and perfluoro N-butylpiperidine; and a perfluoro N-$C_{5-7}$-alkylmorpholine such as perfluoro N-pentylmorpholine, perfluoro N-hexylmorpholine and perfluoro N-heptylmorpholine.

When a perfluoro combination including a tertiary amine is used, the ratio of the (non-tertiary amine) perfluorocarbon compound to the perfluoro tert-amine to be used is 50:95 to 50:5 by weight and the total amount of perfluorocarbon compound and perfluoro tert-amine contained in an emulsion is about 10 to 50% (W/V).

Where emulsions are employed, suitable adjuvants for preparing stable perfluorocarbon emulsions as known in the art are employed. For example, perfluorocarbon emulsions are known containing as emulsifying adjuvants a high molecular weight nonionic surfactant having a molecular weight of about 2,000 to 20,000, a phospholipid and at least one fatty acid compound selected from fatty acids having 8 to 22 carbon atoms, physiologically acceptable salts thereof or monoglyceride thereof.

The high molecular weight nonionic surfactant has a molecular weight of about 2,000 to about 20,000 and includes polyoxyethylene-polyoxypropylene copolymers, polyoxyethylene alkyl ethers and polyoxyethylene alkylaryl ethers. The concentration of said surfactant in the emulsion is about 2.0% to about 5.0%, preferably from about 3.0% to about 3.5%. (Unless indicated otherwise, all percentages refer to the amount proportion of a material by weight (e.g., grams) based on 100 ml of the resulting emulsion.)

The phospholipids used as emulsifier adjuvant in the invention are ones commonly used in the art, and those comprising yolk phospholipid or soybean phospholipid are preferable. The amount present in the emulsion ranges from about 0.1 to about 1.0% (W/V), and preferably about 0.4 to about 0.6% (W/V).

The fatty acid compound used as emulsifying adjuvant is a fatty acid having 8 to 22 carbon atoms, a physiologically acceptable salt such as sodium or potassium salt or a monoglyceride thereof, which includes, for example, caprylic acid, capric acid, lauric acid, myristic acid, palmitic acid, stearic acid, behenic acid, palmitoleic acid, oleic acid, linoleic acid, arachidonic acid and sodium or potassium salt and monoglyceride thereof. These fatty acid compounds may be used alone or as a mixture of two or more kinds thereof in such a minor amount of 0.004 to 0.1% (W/V), and preferably about 0.02 to 0.04% (W/V).

A preferred group of emulsions useable herein contain at least one perfluorocarbon compound having a particle size of about 0.05 μm to about 0.3 μm, which comprises at least one perfluorocarbon compound having 9 to 11 carbon atoms selected from perfluorodecalin, perfluoromethyldecalin, perfluoroalkylcyclohexanes having 3 to 5 carbon atoms in the alkyl, perfluoroalkyltetrahydrofurans having 5 to 7 carbon atoms in the alkyl, perfluoroalkyltetrahydropyrans having 4 to 6 carbon atoms in the alkyl or perfluoroalkanes having 9 to 11 carbon atoms; at least one perfluorotert-amine having 9 to 11 carbon atoms selected from perfluorotert-alkylamines having 9 to 11 carbon atoms, perfluoro-N-alkylpiperidines having 4 to 6 carbon atoms in the alkyl or perfluoro-N-alkylmorpholines having 5 to 7 carbon atoms in the alkyl; a high molecular weight nonionic surfactant having a molecular weight of about 2,000 to about 20,000; a phospholipid; and at least one fatty acid compound selected from fatty acids having 8 to 22 carbon atoms, physiologically acceptable salts thereof or monoglycerides thereof; wherein the ratio of said perfluorocarbon compound to said perfluorotert-amine is 95–50:5–50 by weight.

An example of a perfluorochemical emulsion that can be used according to a method of the present invention is Fluosol® (Green Cross Corporation, Osaka, Japan), which is a sterile, isotonic perfluorochemical emulsion consisting of perfluorodecalin and perfluoro-tri-n-propylamine. The emulsion must be stored in a frozen state (−5° C. to −30° C.) prior to use. Fluosol® is prepared from a perfluorochemical stem emulsion which contains the following compounds:

perfluorodecalin in an amount of about 17.5% weight per volume;
perfluorotri-n-propylamine in an amount of about 7.5% weight per volume;
Poloxamer 188® in an amount of about 3.4% weight per volume;
egg yolk phospholipids (a mixture of naturally occurring phospholipids isolated from egg yolk) in an amount of about 0.5% weight per volume;
potassium oleate in an amount of about 0.040% weight per volume;
glycerol in amount of about 1.0% weight per volume; and
water as the remaining portion to make a total of about 100%.

The average particle diameter of Fluosol® emulsified perfluorochemical particles as determined by a laser light scattering method is less than 270 nanometers.

Poloxamer 188® is a polyoxyethylene-polyoxypropylene copolymer surfactant of about 8350 molecular weight. The structure of Poloxamer 188® is:

HO—(CH$_2$CH$_2$O)$_a$—[CH(CH$_3$)(CH$_2$O)]$_b$—(CH$_2$CH$_2$O)$_c$—H where values for a, b and c are approximately 74, 31 and 74, respectively. The structures of remaining constituents are well known.

Additional solution(s) can be added to the stem emulsion to make a final 20% emulsion and which serve to adjust pH, ionic strength and osmotic pressure, where desired. Examples of suitable additive solutions include the following additive solutions I and II, in combination:

| Ingredient | Amount (% w/v) |
|---|---|
| ADDITIVE SOLUTION I | |
| Sodium Bicarbonate | 3.5 |
| Potassium Chloride | 0.56 |
| Water | q.s. |
| ADDITIVE SOLUTION II | |
| Sodium Chloride | 4.29 |
| Dextrose | 1.29 |
| Magnesium Chloride | 0.305 |
| Calcium Chloride | 0.254 |
| Water | q.s. |

The bag, formed of a suitable gas permeable/liquid impermeable membrane, in collapsed form can be inserted into the intestinal tract or peritoneal cavity employing various known techniques. For example, in one form of the invention, the collapsed balloon is introduced into the stomach via a nasogastric tube, or into the peritoneal cavity via a small laparoscopic incision.

The bag volume will vary depending upon where it is inserted. For example, for use within the average size adult human stomach, bags of about 250 to 1,000 ml internal volume can be employed. Smaller or larger size bags can be employed in other areas in the body and can also be appropriately shaped so as to conform to the shape of the cavity into which inserted, when inflated by introduction of a liquid perfluoro-chemical into the bag.

Prior to use, an appropriate valve needs to be placed in sealing relationship with the mouth or neck of the bag. The valve must be of a two-way type to allow liquid to be both introduced into and withdrawn from the bag. It is possible to use a one-way valve where there is also an exit orifice in the bag whereby a second one-way valve is placed for withdrawing the liquid perfluorocarbon. This type of approach would be especially useful in a continuous, circulating system. Also, a fill tube is inserted through the mouth of the balloon to an appropriate location allowing the introduction and/or withdrawal of the liquid perfluorocarbon. In one embodiment of the invention, the tube and valve are a single unit inserted into the bag together. The bag is preferably of a flexible material allowing it to be wrapped around the fill tube for ease of insertion into the body.

Following usage, the balloon is extracted from the body after essentially collapsing it or, alternatively, the perfluorocarbon liquid is withdrawn, the fill tube is extracted and the collapsed balloon with closed valve in place is allowed to pass through the rectum.

Prior to use, the perfluorocarbon liquid is saturated with oxygen using any technique known in the art. For example, see U.S. Pat. No. 4,769,241 by Heldebrant, et al. Thereafter, the perfluorochemical liquid is introduced into the bag via the fill tube and is allowed to remain in place until its pO$_2$ has fallen to a level which does not allow for continued oxygen transmission from the fluid to either the gastric mucosa or the peritoneal surface. At this time, the fluid is drained and re-oxygenated and treated in such a manner, such as by agitation, to allow any CO$_2$ to diffuse out to the emulsion. Following re-oxygenation and removal of CO$_2$, the emulsion is again reinfused into the membrane bag located within the stomach or the peritoneal cavity. In a further modification of the invention, there could be alternate "reservoirs" of emulsion so that when the first "reservoir" has been introduced into the body, a second reservoir could be undergoing the oxygenation and removal of $CO_2$. When the first reservoir within the body has completed the gas exchange process, it could be removed and the second reservoir inserted. The processes on the first and second reservoir could then be alternated.

In theory, this same technique could be used to supply oxygen to the entire gastrointestinal tract. It is, however, recognized that it may be difficult to insert an appropriate membrane balloon throughout the entire length of the small and large intestine.

In a further modification of the procedure, the membrane inserted into the body cavity would be permeable to glucose, electrolytes, and/or amino acids as well as oxygen and $CO_2$. In this way, the long term metabolic needs of the cells could be met as well as the oxygenation and removal of $CO_2$. These nutrients and electrolytes can be conveniently added as adjunct solutions to known perfluorocarbon emulsions.

The $pO_2$ and $pCO_2$ of the perfluorocarbon liquid can be measured in various ways. Continuous or discontinuous analysis of small volumes of sample liquid withdrawn via the fill tube can be carried out.

Variations of the invention will be apparent to the skilled artisan. For example, a continuous recirculatory system could be employed where spent perfluorochemical liquid is continuously withdrawn from the bag and freshly oxygenated perfluorocarbon liquid is continuously introduced into the bag.

What is claimed is:

1. A method for providing oxygen internally to a mammal which comprises introducing an oxygenated liquid perfluorochemical enclosed within an oxygen permeable/perfluorochemical impermeable membrane into an internal body cavity of said mammal and releasing oxygen through said membrane into said body cavity.

2. The method of claim 1, wherein the body cavity is within the gastrointestinal tract of the mammal.

3. The method of claim 1, wherein the body cavity is the peritoneal cavity.

4. The method of claim 1, wherein the body cavity is the stomach.

5. The method of claim 1, wherein the concentration of oxygen within the membrane is monitored continuously or discontinuously.

6. The method of claim 5, wherein oxygen partial pressure is monitored.

7. The method of claim 1, wherein liquid perfluorochemical is withdrawn from said enclosed membrane, re-oxygenated and reintroduced into said membrane.

8. The process of claim 7, which is carried out continuously.

9. The process of claim 7, which is carried out discontinuously.

10. The method of claim 1, wherein said liquid perfluorochemical includes at least one additive which can also permeate through the membrane into the cavity.

11. The method of claim 10, wherein said additive is a sugar, an electrolyte or an amino acid.

12. The method of claim 10, wherein said additive is a drug.

13. The method of claim 1, wherein said liquid perfluorochemical is emulsified in water.

* * * * *